US010364730B2

(12) United States Patent
Uchiyama et al.

(10) Patent No.: US 10,364,730 B2
(45) Date of Patent: Jul. 30, 2019

(54) SENSOR (71) Applicant: ISUZU MOTORS LIMITED, Tokyo (JP)

(72) Inventors: Tadashi Uchiyama, Fujisawa (JP); Naoto Murasawa, Fujisawa (JP); Satoshi Hanawa, Fujisawa (JP)

(73) Assignee: ISUZU MOTORS LIMITED, Tokyo (JP)

( * ) Notice: Subject to any disclaimer, the term of this patent is extended or adjusted under 35 U.S.C. 154(b) by 253 days.

(21) Appl. No.: 15/321,446

(22) PCT Filed: Jun. 11, 2015

(86) PCT No.: PCT/JP2015/066895
§ 371 (c)(1),
(2) Date: Dec. 22, 2016

(87) PCT Pub. No.: WO2015/198884
PCT Pub. Date: Dec. 30, 2015

(65) Prior Publication Data
US 2017/0159536 A1  Jun. 8, 2017

(30) Foreign Application Priority Data

Jun. 23, 2014  (JP) .................................. 2014-128599

(51) Int. Cl.
*F01N 11/00* (2006.01)
*F01N 3/023* (2006.01)
(Continued)

(52) U.S. Cl.
CPC ............ *F01N 11/007* (2013.01); *F01N 3/023* (2013.01); *F01N 3/027* (2013.01);
(Continued)

(58) Field of Classification Search
CPC ............ B01D 46/0063; B01D 46/2403; F01N 2550/04; F01N 2560/05; F01N 2560/20;
(Continued)

(56) References Cited

U.S. PATENT DOCUMENTS 3,226,615 A  *  12/1965  Nagel ....................... B03C 3/68
324/690
4,158,610 A  *  6/1979  Bauer ...................... C10B 43/00
201/1

(Continued)

FOREIGN PATENT DOCUMENTS

CN       103502588 A       1/2014
JP       H6-257422         9/1994
(Continued)

OTHER PUBLICATIONS

JPO English machine translation of JP 2003-098135, dated 2003.*
(Continued)

*Primary Examiner* — John Fitzgerald
(74) *Attorney, Agent, or Firm* — Procopio, Cory, Hargreaves & Savitch LLP (57) ABSTRACT The PM sensor includes: a filter member having a plurality of measuring cells which are defined by a porous partition wall and configured to trap particulate matter in exhaust gas; at least a pair of electrode members which are disposed to face each other with the measuring cell sandwiched therebetween to form a condenser; a heater member which heats the measuring cell to burn and remove particulate matter accumulated in the measuring cell; and an estimation unit which estimates an amount of the particulate matter contained in the exhaust gas based on an electrostatic capacity between the pair of electrode members.

5 Claims, 6 Drawing Sheets (51) Int. Cl.
| | | |
|---|---|---|
| G01N 27/22 | (2006.01) | |
| F01N 3/027 | (2006.01) | |
| G01N 15/06 | (2006.01) | |
| G01N 27/60 | (2006.01) | |
| B01D 46/42 | (2006.01) | |
| B01D 46/00 | (2006.01) | |
| B01D 46/24 | (2006.01) | |
| G01N 1/22 | (2006.01) | |

(52) U.S. Cl.
CPC ..... *G01N 15/0618* (2013.01); *G01N 15/0656* (2013.01); *G01N 27/22* (2013.01); *G01N 27/60* (2013.01); *B01D 46/0063* (2013.01); *B01D 46/2403* (2013.01); *B01D 46/42* (2013.01); *B01D 2279/30* (2013.01); *F01N 2550/04* (2013.01); *F01N 2560/05* (2013.01); *F01N 2560/20* (2013.01); *G01N 1/2205* (2013.01); *G01N 27/221* (2013.01)

(58) Field of Classification Search
CPC ..... F01N 3/023; F01N 3/027; G01N 15/0618; G01N 15/0656; G01N 1/2205; G01N 27/22; G01N 27/221
See application file for complete search history.

(56) References Cited

U.S. PATENT DOCUMENTS

| | | | | |
|---|---|---|---|---|
| 4,283,207 | A * | 8/1981 | Martyniuk | F01N 3/021 55/282 |
| 4,404,795 | A * | 9/1983 | Oishi | F01N 3/027 55/282 |
| 4,427,418 | A * | 1/1984 | Kogiso | F01N 3/027 422/178 |
| 4,656,832 | A | 4/1987 | Yukihisa et al. | |
| 5,250,094 | A * | 10/1993 | Chung | B01D 39/202 55/523 |
| 5,423,904 | A * | 6/1995 | Dasgupta | B01D 46/0023 55/282 |
| 6,024,927 | A | 2/2000 | Ban et al. | |
| 6,772,584 | B2 * | 8/2004 | Chun | B01D 53/9431 60/275 |
| 7,469,532 | B2 * | 12/2008 | Williamson | F01N 3/0222 55/282.2 |
| 7,574,895 | B2 * | 8/2009 | Schnell | G01N 15/0656 73/28.01 |
| 8,210,033 | B2 * | 7/2012 | Kondo | F01N 9/002 73/114.69 |
| 8,225,684 | B2 * | 7/2012 | Kondo | B01D 46/0086 210/85 |
| 8,382,884 | B2 * | 2/2013 | Okayama | G01N 27/226 60/275 |
| 8,549,846 | B2 * | 10/2013 | Gonze | F01N 3/027 60/295 |
| 8,679,413 | B2 * | 3/2014 | Ishihara | B01J 19/2485 422/174 |
| 9,151,205 | B2 * | 10/2015 | Huq | F01N 11/00 |
| 9,915,597 | B2 * | 3/2018 | Noda | G01N 15/0656 |
| 2008/0087007 | A1 * | 4/2008 | Konstandopoulos | B01D 46/0063 60/286 |
| 2012/0076699 | A1 * | 3/2012 | Ishihara | B01J 19/2485 422/174 |
| 2012/0103057 | A1 | 5/2012 | Kimata et al. | |
| 2014/0157881 | A1 | 6/2014 | Noda et al. | |
| 2014/0230532 | A1 * | 8/2014 | Huq | F01N 11/00 73/114.69 |
| 2016/0047731 | A1 * | 2/2016 | Noda | G01N 15/0656 73/23.33 |
| 2016/0047732 | A1 * | 2/2016 | Uchiyama | G01N 15/0656 73/23.33 |
| 2017/0226949 | A1 * | 8/2017 | Uchiyama | F02D 41/1466 |
| 2017/0328259 | A1 * | 11/2017 | Uchiyama | F01N 3/18 |
| 2018/0038251 | A1 * | 2/2018 | Uchiyama | F01N 3/023 |
| 2018/0038817 | A1 * | 2/2018 | Uchiyama | G01N 27/22 |

FOREIGN PATENT DOCUMENTS

| | | |
|---|---|---|
| JP | 2003-098135 A | 4/2003 |
| JP | 2003201823 A | 7/2003 |
| JP | 2009-097410 A | 5/2009 |
| JP | 2012-083210 A | 4/2012 |
| JP | 2012-093287 A | 5/2012 |
| JP | 2012-117383 A | 6/2012 |
| JP | 2012-241643 A | 12/2012 |
| JP | 2013-205034 A | 10/2013 |
| WO | 2012160950 A1 | 11/2012 |
| WO | 2014129447 A1 | 8/2014 |

OTHER PUBLICATIONS

Office Action for Japanese Patent Application No. 2014-128599 dated Oct. 24, 2017; 8 pages. Computer generate English translation provided.
Notification of Reasons for Refusal for Japanese App No. 2014-128599 dated May 22, 2018, 6 pgs.
Extended European Search Report for EP App No. 15811540.2 dated Mar. 2, 2018, 7 pgs.
International Search Report and Written Opinion for PCT App No. PCT/JP2015/066895 dated Sep. 8, 2015, 9 pgs.
Office Action for related CN Patent Application No. 201580033488.0, dated Feb. 2, 2019, in 14 pages.

* cited by examiner

SENSOR

CROSS-REFERENCE TO RELATED APPLICATIONS

This application is a U.S. National Stage entry of PCT Application No. PCT/JP2015/066895, filed on Jun. 11, 2015, which claims priority to JP App No: 2014-128599, filed Jun. 23, 2014. The contents of the foregoing are incorporated by reference.

TECHNICAL FIELD

The present invention relates to a sensor and more particularly to a PM sensor which detects a particular matter (hereinafter, referred to as PM) which is contained in exhaust gas.

BACKGROUND ART

Conventionally, an electric resistance-type PM sensor has been known as a sensor which detects PM in exhaust gas discharged from an internal combustion engine. In a general electric resistance-type PM sensor, a pair of conductive electrodes are disposed in a face-to-face fashion on a surface of an insulated substrate, so that a PM amount is estimated by making use of the fact that an electric resistance value changes due to conductive PM (mainly, a soot component) adhering to these electrodes (for example, refer to Patent Literature 1).

PRIOR ART LITERATURE

Patent Literature

Patent Literature 1: JP-A-2012-83210

SUMMARY OF THE INVENTION

Problem that the Invention is to Solve

Incidentally, the electric resistance-type PM sensor has a simple construction in which PM is caused to adhere to each electrode. Therefore, in particular, under operating conditions where a flow rate of exhaust gas is increased, there is a possibility that part of the PM adhering to the electrodes may come off, leading to a problem that the estimation accuracy cannot be ensured. In addition, since the electric resistance of the PM adhering to the electrodes may change when it is subjected to the influence of the flow rate of exhaust gas, there is caused a problem that the PM amount cannot be estimated accurately. Further, an electric resistance value between the electrodes does not change until the electrodes are connected to each other by the accumulated PM. Owing to this, the amount of PM discharged from the engine cannot be estimated in real time, and hence, there is caused a problem that the application of the electric resistance-type PM sensor is limited to the on-board diagnosis of a failure in a position lying downstream of a diesel particulate filter (hereinafter, referred to as DPF).

An object of the invention is to provide a PM sensor which can estimate an amount of PM contained in exhaust gas in real time while reducing a regeneration time effectively.

Means for Solving the Problem

With a view to achieving the object described above, according to the invention, there is provided a sensor including: a filter member having a plurality of cells which are defined by a porous partition wall and configured to trap particulate matter in exhaust gas; at least a pair of electrode members which are disposed to face each other with the cell sandwiched therebetween to form a condenser; a heater member which heats the cell to burn and remove particulate matter accumulated in the cell; and an estimation unit which estimates an amount of the particulate matter contained in the exhaust gas based on an electrostatic capacity between the pair of electrode members.

The heater member may be a heating wire which is inserted into the cell and which is energized to be heated.

The filter member may be a filter layer in which the plurality of cells are disposed in parallel in one direction, the pair of electrode members may be first and second planar electrode plates which are disposed to face each other with the filter layer sandwiched therebetween, the heater member may be a planar heater substrate which is energized to be heated, and the heater substrate may be interposed either between the first electrode plate and the filter layer or between the second electrode plate and the filter layer.

The sensor may further include a filter regeneration control unit which executes a filter regeneration control in which, when the amount of particulate matter accumulated in the cells reaches a predetermined upper limit value, the accumulated particulate matter are burnt by the heater member and removed, and the estimation unit may estimate the amount of the particulate matter in real time by integrating regeneration interval periods from an end of a filter regeneration control to a start of a next filter regeneration control.

The estimation unit may estimate a momentary amount of particulate matter in real time based on a variation in electrostatic capacity per unit time between the electrode members.

BRIEF DESCRIPTION OF DRAWINGS

In FIG. 5, (A) is a schematic perspective view showing a sensor unit according to the second embodiment, and (B) is a schematic exploded perspective view showing the sensor unit according to the second embodiment.

MODE FOR CARRYING OUT THE INVENTION

Hereinafter, PM sensors according to embodiments of the invention will be described based on the accompanying drawings. Same reference numerals will be given to same parts, and their designations and functions are also the same. Therefore, detailed descriptions of such parts will not be repeated.

First Embodiment

Figure 1:
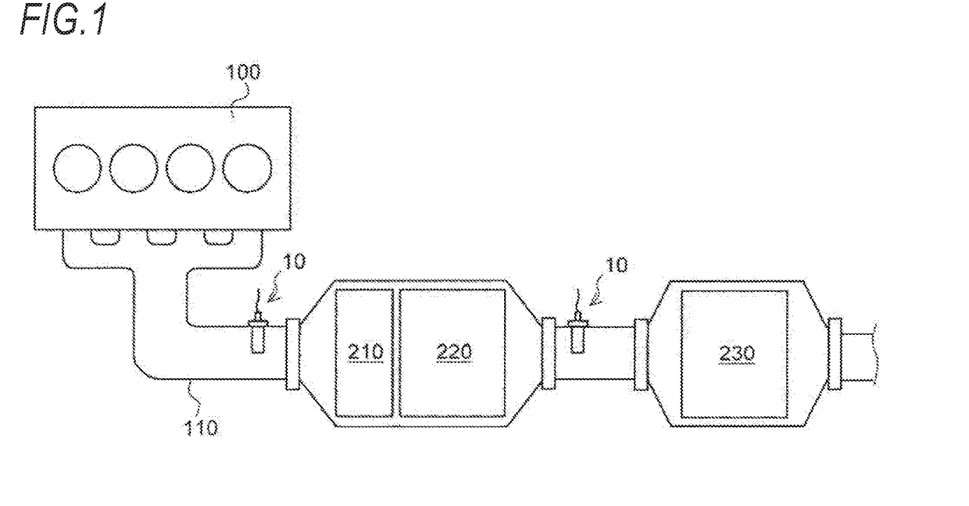
FIG. 1 is a schematic block diagram showing an example of an exhaust system to which a PM sensor of a first embodiment is applied.

FIG. 1 is a schematic block diagram showing an example of an exhaust system of a diesel engine (hereinafter, referred to simply as an engine) 100 to which a PM sensor 10 of a first embodiment is applied. An oxidation catalyst 210, a DPF 220, a NOx removal catalyst 230 and the like are provided sequentially in that order from an upstream side of a flow of exhaust gas in an exhaust pipe 110 of the engine 100. The PM sensor 10 of this embodiment may be provided, for example, either in a portion of the exhaust pipe 110 which lies upstream of the DPF 220 or in a portion of the exhaust pipe 110 which lies downstream of the DPF 220.

Figure 2:
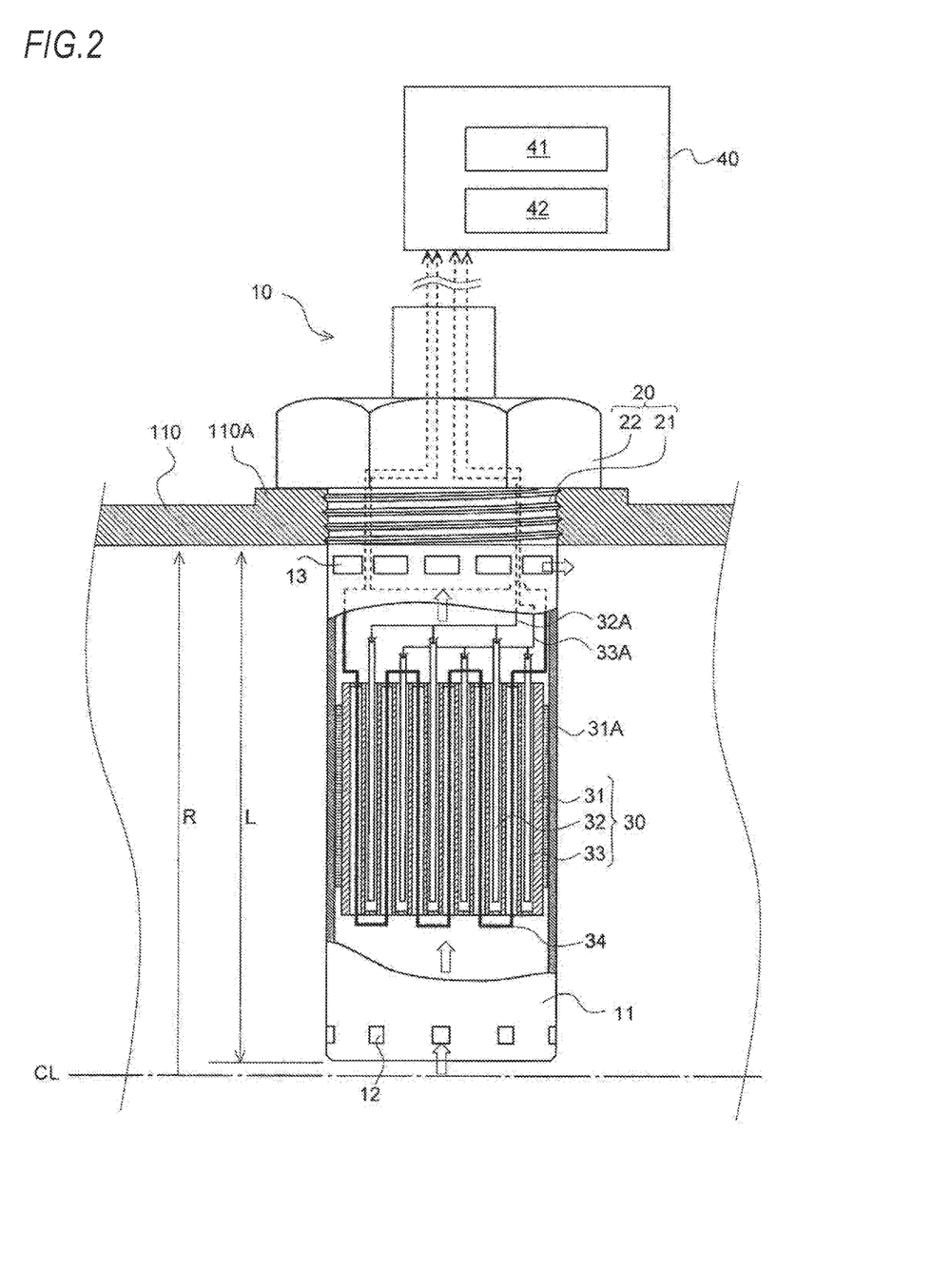
FIG. 2 is a schematic partial sectional view showing the PM sensor of the first embodiment.

Next, a detailed configuration of the PM sensor 10 according to the first embodiment will be described based on FIG. 2.

The PM sensor 10 includes a case member 11 which is inserted in an interior of the exhaust pipe 110, a seat portion 20 where the case member 11 is attached to the exhaust pipe 110, a sensor unit 30 which is accommodated in the case member 11, and a control unit 40.

The case member 11 has a bottomed cylindrical shape which is closed on a bottom portion side (a lower end side in the illustrated example). A length L in an axial direction of the case member 11 is made to be substantially the same length as a radius R of the exhaust pipe 110 so that a cylindrical wall portion on the bottom portion side protrudes as far as the vicinity of an axis center CL of the exhaust pipe 110. In the following description, the bottom portion side of the case member 11 will be referred to as a distal end side, and an opposite side to the bottom portion side will be referred to as a proximal end side of the case member 11.

A plurality of inlet ports 12 are provided circumferentially at certain intervals in a cylindrical wall portion of the case member 11 on the distal end side thereof. A plurality of outlet ports 13 are provided circumferentially at certain intervals in a cylindrical wall portion of the case member 11 on the proximal end side thereof. A total opening area $S_{12}$, of the inlet ports 12 is made to be smaller than a total opening area $S_{13}$ of the outlet ports 13 ($S_{12} < S_{13}$). Namely, a flow velocity $V_{12}$ of exhaust gas near the inlet ports 12 becomes slower than a flow velocity $V_{13}$ of exhaust gas near the outlet ports 13 ($V_{12} < V_{13}$), whereby a pressure $P_{12}$ on the side where the inlet ports 12 are provided becomes higher than a pressure $P_{13}$ on the side where the outlet ports 13 are provided ($P_{12} > P_{13}$). By doing so, exhaust gas is taken smoothly into the case member 11 from the inlet ports 12, and at the same time, the exhaust gas inside the case member 11 is discharged smoothly from the outlet ports 13 into the exhaust pipe 110.

The seat portion 20 includes an external thread portion 21 and a nut portion 22. The external thread portion 21 is provided at a proximal end portion of the case member 11 and closes an opening portion at the proximal end side of the case member 11. This external thread portion 21 is screwed into an internal thread portion of a boss portion 110A which is formed on the exhaust pipe 110. The nut portion 22 is, for example, a hexagon nut and is fixed to an upper end portion of the external thread portion 21. A through hole (not shown) is formed in the external thread portion 21 and the nut portion 22 for passage of conductive wires 32A, 33A, which will be described later, and the like.

The sensor unit 30 includes a filter member 31, a plurality of pairs of electrodes 32, 33 and an electric heater 34.

The filter member 31 is made up, for example, of a plurality of cells which are defined by porous ceramic partition walls and serve as exhaust gas flow paths arranged in a grid-like fashion with upstream sides and downstream sides of the cells being plugged alternately. This filter member 31 is held on an inner circumferential wall of the case member 11 via a cushion member 31A with the exhaust gas flow paths of the cells directed substantially parallel to the axial direction (a vertical direction in the figure) of the case member 11. PM in exhaust gas taken into the case member 11 from the inlet ports 12 are trapped on surfaces of the partition walls or in fine holes by allowing the exhaust gas so taken in to flow from the cell which is plugged at the downstream side thereof into the cell which is plugged at the upstream side thereof. In the following description, the cells which are plugged at the downstream side will be referred to as measuring cells, and the cells which are plugged at the upstream side will be referred to as electrode cells.

The electrodes 32, 33 are, for example, conductive metallic wires and are inserted alternately into the electrode cells which face each other with the measuring cell sandwiched therebetween from the downstream sides (the sides which are not plugged) to form the condenser. These electrodes 32, 33 are connected to an electrostatic capacity detection circuit, not shown, which is incorporated in the control unit 40 via conductive wires 32A, 33A, respectively.

The electric heater 34 is, for example, a heating wire and executes a so-called filter regeneration in which the electric heater 34 is energized to be heated so as to heat directly the measuring cells so that PM accumulated within the measuring cells are burnt and removed. Owing to this, the electric heater 34 is bent so as to form continuous S-like shapes and is inserted into the measuring cells in such a way that straight-line portions which are parallel to each other extend along the flow paths of the measuring cells.

The control unit 40 includes a filter regeneration control unit 41 and a PM amount estimation and calculation unit 42 as functional elements. These functional elements will be described as being incorporated in the control unit 40 which is integral hardware. However, the functional elements can also be provided in separate pieces of hardware.

The filter regeneration control unit 41 executes a filter regeneration control in which the electric heater 34 is switched on (energized) based on an electrostatic capacity Cp between the electrodes 32, 33, which is detected by the electrostatic capacity detection circuit (not shown). The electrostatic capacity Cp between the electrodes 32, 33 is expressed by the following expression 1 where a dielectric constant of a medium between the electrodes 32, 33 is ε, a surface area of the electrodes 32, 33 is S, and a distance between the electrodes 32, 33 is d.

$$Cp = \sum \left( \varepsilon \times \frac{S}{d} \right) \qquad \text{[Expression 1]}$$

Figure 3:
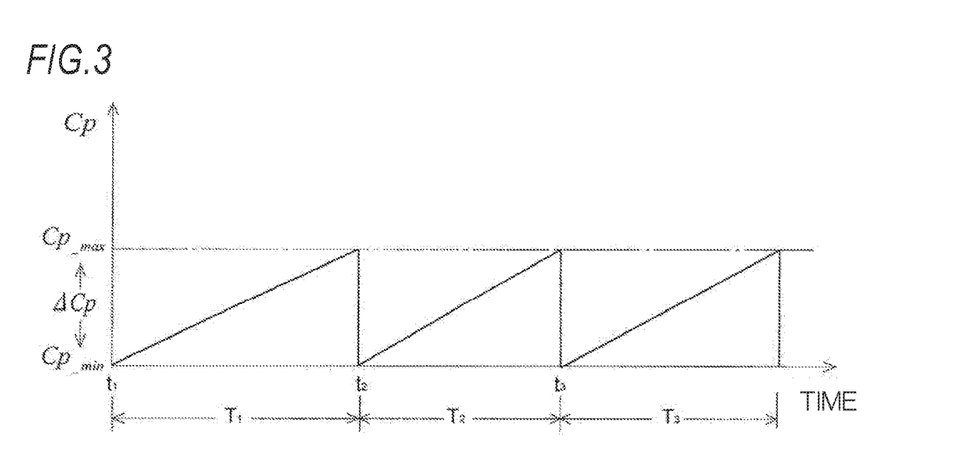
FIG. 3 is a timing chart illustrating a filter regeneration according to the first embodiment.

In Expression 1, the surface areas of the electrodes 32, 33 is constant, and when the dielectric constant ε and the distance d are changed by PM trapped in the measuring cell, the electrostatic capacity Cp is also changed in association with the changes in the dielectric constant ε and the distance d. Namely, a proportional relation is established between the electrostatic capacity Cp between the electrodes 32, 33 and an amount of PM accumulated on the filter member 31. The filter regeneration control unit 41 starts a filter regeneration in which the electric heater 34 is switched on when the electrostatic capacity Cp between the electrodes 32, 33 reaches a predetermined electrostatic capacity upper limit threshold $Cp_{\_max}$ which indicates a PM upper limit accumulation amount (refer to times $t_1$, $t_2$, $t_3$ in FIG. 3). This filter regeneration continues until the electrostatic capacity Cp is lowered to a predetermined electrostatic capacity lower limit threshold $Cp_{\_min}$ which indicates a complete removal of PM.

The PM estimation and calculation unit 42 estimates a total PM amount $m_{PM\_sum}$ of exhaust gas which is discharged from the engine 100 based on an electrostatic capacity variation $\Delta Cp_n$ during a regeneration interval $T_n$ (from an end of a filter regeneration to a start of the next filter regeneration). A PM amount of PM trapped on the filter member 31 during the regeneration interval $T_n$ is obtained by the following expression 2 in which the electrostatic capacity variation $\Delta Cp_n$ is multiplied by a primary coefficient $\beta$.

$$m_{PM} = \beta \cdot \Delta CP_n \quad \text{[Expression 2]}$$

The PM amount estimation and calculation unit 42 calculates a total PM amount $m_{PM\_sum}$ in exhaust gas discharged from the engine 100 in real time based on the following expression 3 in which PM amounts $m_{PM\_n}$ during each regeneration interval Tn, which are calculated from Expression 2, are integrated sequentially.

$$m_{PM\_sum} = \beta \cdot \Delta Cp_1 + \beta \cdot \Delta Cp_2 + \ldots + \beta \cdot \Delta Cp_n = \beta \cdot \sum_{T=1}^{n} \Delta Cp_T \quad \text{[Expression 3]}$$

Figure 4:
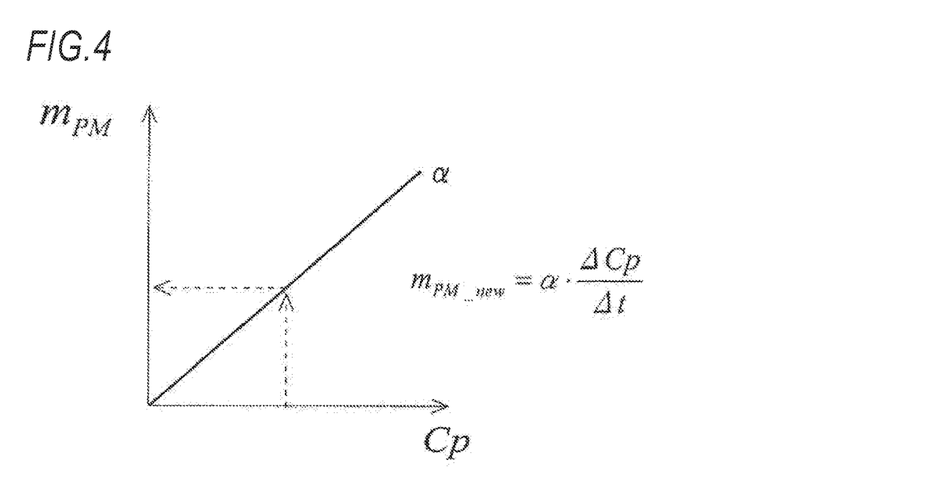
FIG. 4 is a diagram illustrating an example of a map according to the first embodiment.

It is also possible to estimate in real time a momentary PM amount $m_{PM\_new}$ of PM contained in exhaust gas from a variation $\Delta Cp/\Delta t$ in electrostatic capacity Cp per unit time. In this case, a map (refer to FIG. 4) showing a relation between the electrostatic capacity CP and the PM amount $m_{PM}$ which is obtained in advance through experiments and the like is used, and the momentary PM amount $m_{PM\_new}$ can be obtained by multiplying the map by the momentary variation $\Delta Cp/\Delta t$ in electrostatic capacity Cp. In a case where the momentary PM amount $m_{PM\_new}$ is estimated in the way described above, by providing the PM sensor 10 in the portion of the exhaust pipe 110 which lies upstream of the DPF 220, since the momentary PM amount $m_{PM\_new}$ of PM discharged from the engine 100 can be estimated in real time, an engine control such as a smoke limit control can be executed effectively.

Next, working effects of the PM sensor 10 according to this embodiment be described.

In the electric resistance-type PM sensor in which a PM amount is estimated based on an electric resistance value between the electrodes, it becomes difficult for PM accumulated to be kept adhering to the electrodes in an ensured fashion when the flow rate of the exhaust gas is increased, and this causes the problem that the estimation accuracy cannot be ensured. In addition, since the electric resistance of the PM adhering to the electrodes may change when it is subjected to the influence of the flow rate of the exhaust gas, there is caused a problem that the PM amount cannot be estimated accurately. Further, since the electric resistance value between the electrodes does not change until the electrodes are connected to each other by the PM accumulated, there is also caused a problem that the PM amount cannot be estimated in real time.

In contrast with the electric resistance-type PM sensor, the PM sensor 10 of this embodiment calculates in real time a total PM amount $m_{PM\_sum}$ of PM in the exhaust gas discharged from the engine 100 by trapping PM in the exhaust gas by the filter member 31 in an ensured fashion and sequentially integrating PM amounts $m_{PM\_n}$ during each individual regeneration interval $T_n$. Consequently, according to the PM sensor 10 of this embodiment, the total PM amount $m_{PM\_sum}$ of PM discharged from the engine 100 can be estimated highly accurately and in real time. In particular, in case a momentary PM amount $m_{PM\_new}$ is made to be estimated from a variation $\Delta Cp/\Delta t$ in electrostatic capacity per unit time, the engine control can be executed effectively by providing the PM sensor 10 upstream of the DPF 220. In addition, in the case of the PM sensor 10 being provided downstream of the DPF 220, an onboard failure detection of the DPF 220 can be executed highly accurately and early.

With the PM sensor 10 of this embodiment, the electric heater 34 is inserted into the measuring cells so as to heat directly the PM accumulated in the measuring cells at the time of filter regeneration. Consequently, according to the PM sensor 10 of this embodiment, the PM accumulated in the measuring cells can be burnt and removed with good efficiency, thereby making it possible to reduce the filter regeneration time effectively.

Second Embodiment

Next, a PM sensor according to a second embodiment will be described in detail based on FIG. 5. The PM sensor of the second embodiment is such that a laminated sensor unit is used in place of the sensor unit 30 in the first embodiment. The other constituent elements remain the same, and hence, the detailed description and illustration thereof will be omitted here.

Figure 5:
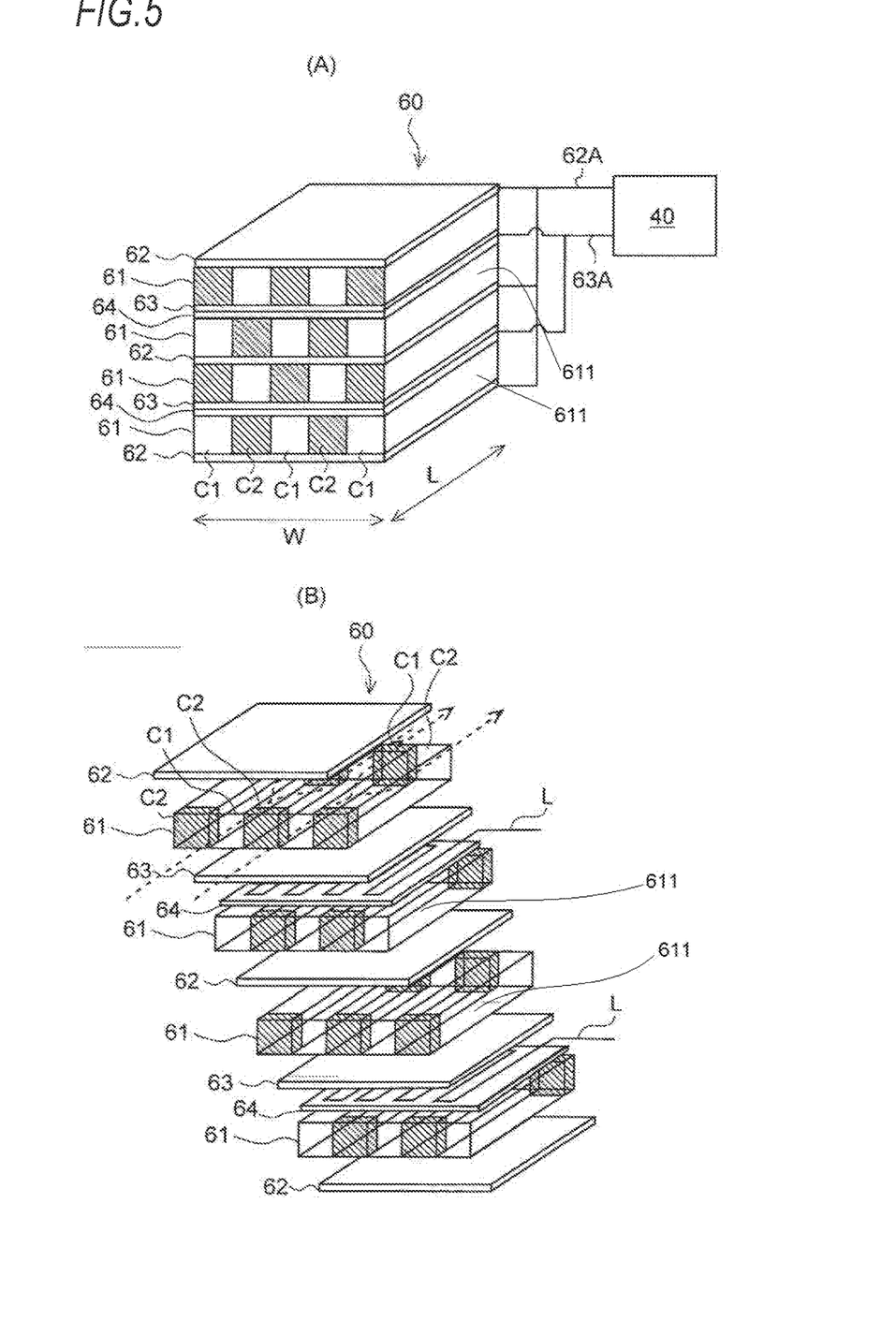

(A) of FIG. 5 is a perspective view of a sensor unit 60 of the second embodiment, and (B) of FIG. 5 is an exploded perspective view of the sensor unit 60. The sensor unit 60 includes a plurality of filter layers 61, pluralities of first and second electrode plates 62, 63, and a plurality of heater substrates 64.

The filter layers 61 each have a rectangular parallelepiped shape in which a plurality of cells are defined by porous ceramic partition walls 611 and serve as an exhaust gas flow path with upstream sides and downstream sides of the cells being plugged alternately and in which the cells are disposed in parallel in one direction. PM contained in exhaust gas is trapped on surfaces of the partition walls 611 or in fine holes of the cell C1 as a result of the exhaust gas flowing from the cell C1 which is plugged at the downstream side thereof into the cell C2 which is plugged at the upstream side thereof, as indicated by arrows at leading ends of broken lines in (b) of FIG. 5. In the following description, a flowing direction of exhaust gas in the exhaust gas flow path in each cell will be referred to as a lengthwise direction (denoted by arrows L in (A) of FIG. 5) of the sensor unit 60 and a direction which is at right angles to the flowing direction of exhaust gas in the exhaust gas flow path will be referred to as a widthwise direction (denoted by arrows W in (A) of FIG. 5) of the sensor unit 60.

The first and second electrode plates 62, 63 are made up of a planar conductive member and are formed so that their external dimensions in the lengthwise direction L and widthwise direction W coincide substantially with those of the filter layer 61. The first and second electrode plates 62, 63 are disposed so as to overlap each other in an alternate fashion with the filter layer 61 sandwiched therebetween and are connected to an electrostatic capacity detection circuit, not shown, which is incorporated in a control unit 40 via conductive wires 62A, 63A, respectively.

Namely, the first electrode plate 62 and the second electrode plate 63 are disposed so as to face each other, and the filter layer 61 is sandwiched between the electrode plates 62, 63, whereby the whole of the cell C1 constitutes a condenser.

In this way, according to the PM sensor of the second embodiment, since whole of the cell C1 is formed to be a condenser by the planar electrode plates 62, 63, an electrode surface area S can be ensured effectively, thereby making it possible to increase a detectable electrostatic capacity absolute value. In addition, a cell pitch becomes an inter-electrode distance d, and hence, the inter-electrode distance d is unified, thereby making it possible to suppress a variation in initial electrostatic capacity effectively.

The heater substrate 64 is made up, for example, of a planar heat-resistant and insulating member with good heat conductivity and is formed so that its external dimensions in the lengthwise direction L and widthwise direction W coincide substantially with those of the filter layer 61. A heating wire L (shown only in (B) of FIG. 5) which is energized to be heated is embedded in an interior of the heater substrate 64 in such a way as to be bent so as to form continuous S-like shapes. In this embodiment, the heater substrate 64 is interposed between the second electrode plate 63 and the filter layer 61.

Namely, when a filter regeneration is executed, the heating wire L is energized to heat directly the interior of the cell C1. By doing so, PM accumulated in the cell C1 can be burnt and removed with good efficiency, whereby the filter regeneration time can be reduced effectively.

The position where the heater substrate 64 is provided is not limited to the position lying between the second electrode plate 63 and the filter layer 61, and hence, the heater substrate 64 may be provided between the first electrode plate 62 and the filter layer 61. In addition, a configuration may be adopted in which with the heater substrate 64 omitted, a voltage is applied directly to the electrode plates 62, 63 when a filter regeneration is executed.

Other Examples

The invention is not limited to the embodiments that have been described heretofore and hence can be carried out by being modified as required without departing from the spirit and scope of the invention.

Figure 6:
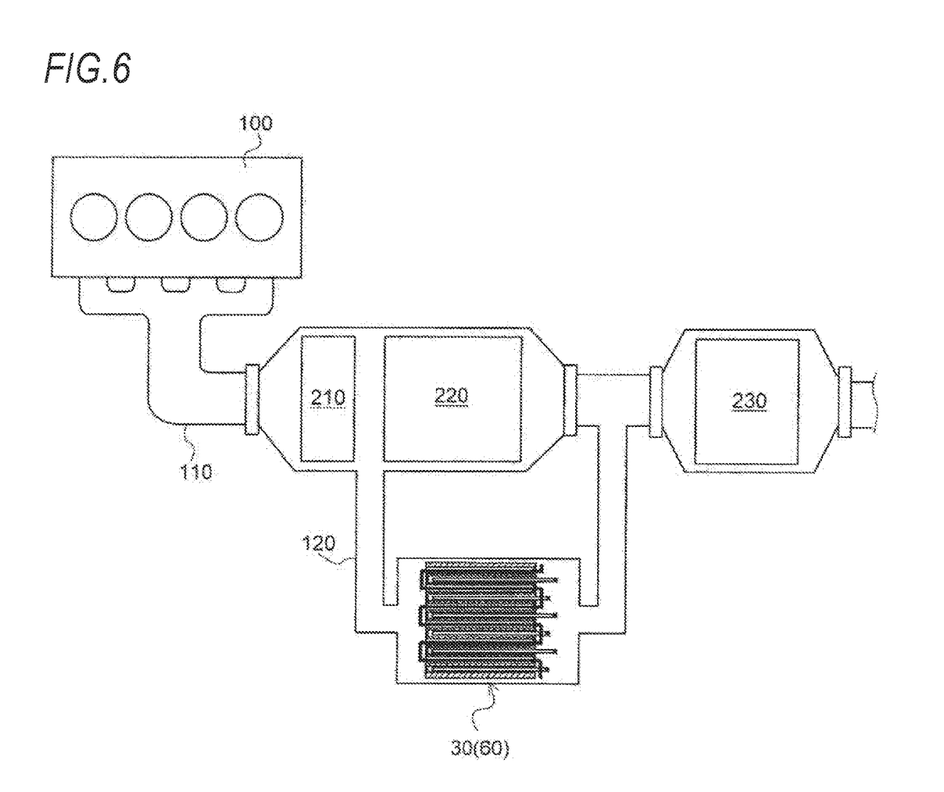
FIG. 6 is a schematic block diagram showing an example of an exhaust system to which a PM sensor of another embodiment is applied.

For example, as shown in FIG. 6, a configuration may be adopted in which a bypass pipe 120 is connected to an exhaust pipe 110 which branches off the exhaust pipe 110 from a position lying between an oxidation catalyst 210 and a DPF 220 and which merges back to the exhaust pipe 110 upstream of a NOx removal catalyst 230, and the sensor unit 30 of the first embodiment or the sensor unit 60 of the second embodiment is disposed within the bypass pipe 120.

Figure 7:
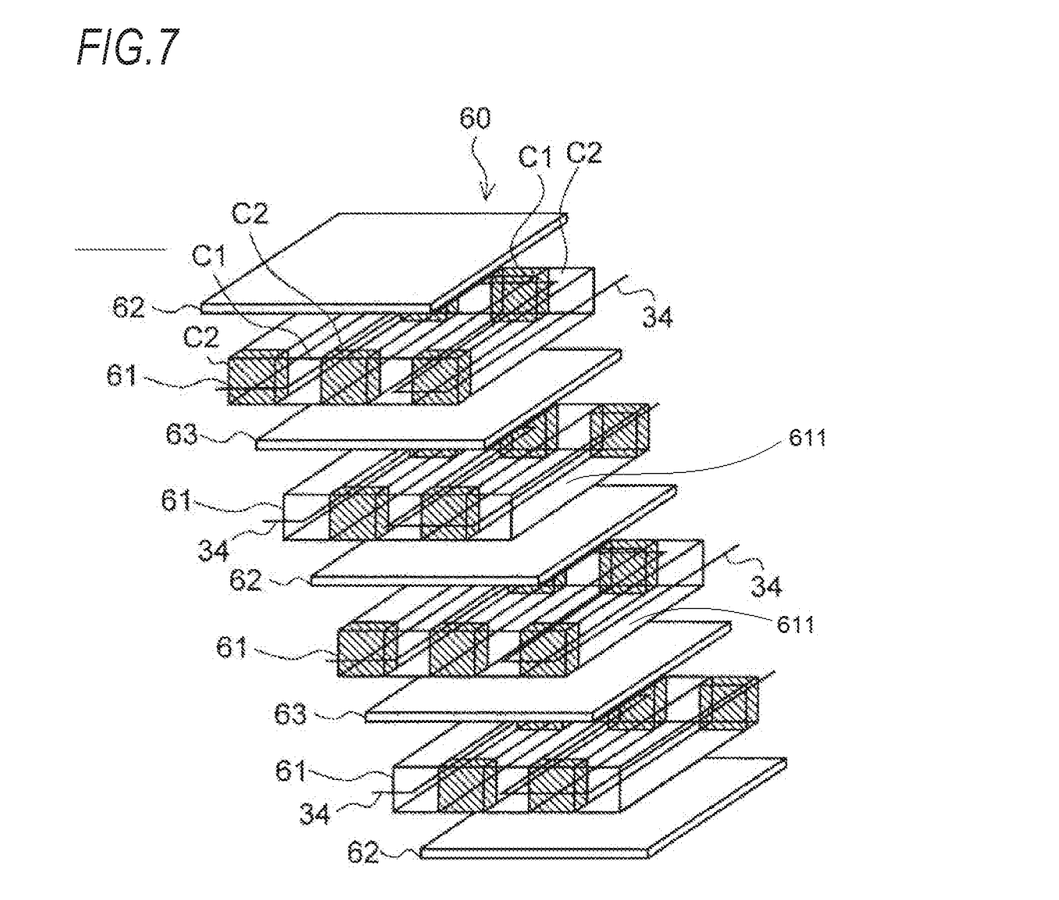
FIG. 7 is a schematic exploded perspective view showing the sensor unit of the other embodiment.

In addition, as shown in FIG. 7, a configuration may be adopted in which the heater substrate 64 of the second embodiment is replaced with the electric heater 34 of the first embodiment.

The invention claimed is:

1. A particulate matter sensor for exhaust gas comprising:
    a filter member having a plurality of cells which are defined by a porous partition wall;
    at least a pair of electrode members which are disposed to face each other with some of the plurality of cells sandwiched therebetween to form a condenser;
    a heater member configured to heat the some of the plurality of cells to burn and remove particulate matter accumulated in some of the plurality of cells;
    an electrostatic capacity detection circuit configured to detect an electrostatic capacity between the pair of electrode members; and
    an estimation unit configured to estimate an amount of the particulate matter contained in the exhaust gas based on the electrostatic capacity between the pair of electrode members detected by the electrostatic capacity detection circuit,
    wherein the filter member is a filter layer in which the plurality of cells are disposed in parallel in one direction,
    wherein the pair of electrode members are first and second planar electrode plates which are disposed to face each other with the filter layer sandwiched therebetween, and
    wherein the heater member is a planar heater substrate which is configured to be energized to be heated, and the planar heat substrate is interposed either between the first planar electrode plate and the filter layer or between the second planar electrode plate and the filter layer along a flow path.

2. The particulate matter sensor according to claim 1, further comprising:
    a filter regeneration control unit configured to execute a filter regeneration process by energizing the heater member in response to the electrostatic capacity between the pair of electrode members detected by the electrostatic capacity detection circuit reaching a predetermined electrostatic capacity upper limit threshold,
    wherein the estimation unit is configured to estimate the amount of the particulate matter in the exhaust gas in real time by calculating an amount of particulate matter trapped by the filter member during a regeneration interval from a variation in the electrostatic capacity detected by the electrostatic capacity detection circuit during the regeneration interval and sequentially adding up the amounts of the particulate matter which are calculated during each regeneration interval.

3. The sensor according to claim 1,
    wherein the estimation unit is configured to estimate a momentary amount of particulate matter in real time based on a variation in the electrostatic capacity detected by the electrostatic capacity detection circuit per unit time.

4. The sensor of claim 1, wherein a first layer of the first planar electrode plate and a second layer of the second planar electrode plate and the heater member are provided alternately between the filter layers.

5. The sensor of claim 1, wherein the heater member and the second planar electrode plate are positioned directly against each other such that opposite faces of the heater member and the second planar electrode plate are facing the flow path.

* * * * *